(12) United States Patent
Campagnolo et al.

(10) Patent No.: US 10,279,109 B2
(45) Date of Patent: May 7, 2019

(54) CLOSED LOOP SYSTEM FOR CONTROLLING THE REFLUX OF A FLUID INJECTION

(71) Applicant: COMMISSARIAT A L'ENERGIE ATOMIQUE ET AUX ENE ALT, Paris (FR)

(72) Inventors: Raymond Campagnolo, Grenoble (FR); Pierre Jallon, Grenoble (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 374 days.

(21) Appl. No.: 14/396,568

(22) PCT Filed: Apr. 23, 2013

(86) PCT No.: PCT/EP2013/058407
§ 371 (c)(1),
(2) Date: Oct. 23, 2014

(87) PCT Pub. No.: WO2013/160312
PCT Pub. Date: Oct. 31, 2013

(65) Prior Publication Data
US 2015/0133889 A1 May 14, 2015

(30) Foreign Application Priority Data
Apr. 23, 2012 (FR) ..................................... 12 53709

(51) Int. Cl.
*A61M 5/142* (2006.01)
*A61M 5/168* (2006.01)

(52) U.S. Cl.
CPC ........ *A61M 5/16854* (2013.01); *A61M 5/142* (2013.01); *A61M 5/14228* (2013.01);
(Continued)

(58) Field of Classification Search
CPC .. A61M 5/142; A61M 5/14228; A61M 5/232; A61M 5/16854; A61M 2205/3331;
(Continued)

(56) References Cited

U.S. PATENT DOCUMENTS 4,534,756 A 8/1985 Nelson
5,292,306 A * 3/1994 Wynkoop ......... A61M 5/16854
417/53

(Continued)

FOREIGN PATENT DOCUMENTS

EP 1 980 201 A2 10/2008
WO WO 2011/058140 A2 5/2011

OTHER PUBLICATIONS

U.S. Appl. No. 13/266,501, filed Feb. 7, 2012, 2012-0128086, Bouzegzi et al.
(Continued)

*Primary Examiner* — Bhisma Mehta
*Assistant Examiner* — Larry R. Wilson
(74) *Attorney, Agent, or Firm* — Oblon, McClelland, Maier & Neustadt, L.L.P.

(57) ABSTRACT

A system for injecting and controlling a flow of liquid to be injected, including: a peristaltic pump; a catheter delivering the liquid to be injected; a pressure sensor measuring liquid pressure in the catheter; a controller receiving data from the pressure sensor and controlling the pump on the basis of the data measured at different times.

13 Claims, 12 Drawing Sheets

(52) U.S. Cl.
CPC ............... *A61M 2205/3331* (2013.01); *A61M 2210/0693* (2013.01)

(58) Field of Classification Search
CPC ...... A61M 2210/0693; A61M 1/14232; A61M 5/14224; A61M 5/14586; A61M 5/16859; A61M 5/6863; A61M 5/16868; A61M 5/16872; A61M 2205/3334; A61M 2205/3341; A61M 2205/3344; A61M 2205/3351; A61M 2205/3355; F04B 43/12–43/1292; F04B 43/14
See application file for complete search history.

(56) References Cited

U.S. PATENT DOCUMENTS

| | | | |
|---|---|---|---|
| 6,558,347 B1 * | 5/2003 | Jhuboo | A61M 5/14228 604/151 |
| 7,794,443 B2 | 9/2010 | Nelson et al. | |
| 2003/0069559 A1 * | 4/2003 | Platt | A61M 5/16854 604/500 |
| 2004/0254514 A1 * | 12/2004 | Gura | A61M 1/16 604/5.01 |
| 2005/0075624 A1 | 4/2005 | Miesel | |
| 2005/0145008 A1 | 7/2005 | Vanderveen et al. | |
| 2007/0274843 A1 | 11/2007 | Vanderveen et al. | |
| 2008/0009837 A1 | 1/2008 | Miesel | |
| 2011/0144540 A1 | 6/2011 | Shen et al. | |
| 2011/0152772 A1 * | 6/2011 | Rotem | A61M 5/14228 604/153 |
| 2011/0208163 A1 | 8/2011 | Miesel | |
| 2011/0257593 A1 | 10/2011 | Kalpin et al. | |
| 2012/0128086 A1 | 5/2012 | Bouzegzi et al. | |

OTHER PUBLICATIONS

French Preliminary Search Report dated Mar. 18, 2013 in Patent Application No. 1253709 (with Translation of Category of cited Documents).

International Search Report dated Jul. 19, 2013, in PCT/EP2013/058407, filed Apr. 23, 2013.

* cited by examiner

CLOSED LOOP SYSTEM FOR CONTROLLING THE REFLUX OF A FLUID INJECTION

TECHNICAL FIELD AND PRIOR ART

The invention relates to the management of the localised injection of a fluid, for example a medical and/or therapeutic fluid.

This is the case especially of the injection of a therapeutic principle into pathological (neuro-degenerative or tumorous) cerebral parenchyma.

It enables the detection of a start of reflux, then to put an end to this start and thereby to assure the safety of a patient. This is because, otherwise, secondary effects can occur, which may be deleterious, an effect, especially, which may be linked to the contamination of the CSF (or Cerebrospinal Fluid).

Document U.S. Pat. No. 7,794,443 describes a device for local delivery of an active principle comprising a tank, a pump and a catheter, all of which are associated with a pressure sensor, a processor and a pressure profile library. It analyses the change over time of the pressure and compares it with a case database (a library of pre-recorded profiles) to determine the state of the infusion. A display system shows the operator the pressure curve over time and indicates whether the delivery is satisfactory or if a problem exists of the type reflux, blocking, presence of air bubbles or rupture of the fluid path.

In this document, the algorithm for selecting the delivery state does not take account of dynamic phenomena affecting the pressure measured and is only based on the final equilibrium state obtained. In the case of reflux, it merely signals that the injection has gone wrong, without any anticipation or preventive action. It is therefore a slow system, in open loop: the measurement of the pressure does not interact on the operation of the pump. The measurements are used a posteriori to monitor the delivery, for example by manually stopping the injection. This measurement does not serve to act automatically on the pump, during delivery. Moreover, only the operator can intervene on the unfolding of the experience. The curves presented in this document have been obtained on a healthy animal brain (sheep), for which the question of heterogeneity of the pathological tissues is not broached, nor is the notion of the dynamic behaviour of the system.

Another document, U.S. Pat. No. 4,534,756, describes a system for analysing pressure associated with an infusion pump and with a control instrument for detecting dysfunctions (such as an infiltration, and/or the open state of a fluid circuit, and/or the presence of air bubbles) in the injection of an active substance, in parenteral mode, in order to generate an alarm.

But this document does not resolve the problems of reflux.

Document EP1980201 describes the different causes, including this time the heterogeneity of the tumorous tissues, affecting the quality of the delivery of therapeutic liquid for the treatment of glioblastoma. In particular, the constitution of the catheter and parameters such as the hydraulic conductivity of the tissues are put forward, and a model of the propagation of the treatment in cerebral parenchyma is presented. The procedure for implanting the catheter is cited as a possible cause of initiation of the reflux (creation of an inter-space around the catheter which encourages the escape of the liquid through its low hydraulic impedance). Software makes it possible to aid, by MRI imaging, the placement of the catheter, at the correct distance from cavities or structures such as cerebral ventricles or grooves that risk leading to a leak of the therapeutic principle, thereby reducing almost to nothing the efficacy of the anti-tumour therapy.

The article "Focal delivery during direct infusion to brain: role of flow rate, catheter diameter and tissue mechanics" by Paul F. Morrison et al., sets out the bases of a mathematical model for the delivery of an active principle from a catheter and gives examples of refluxes that have occurred following a liquid flow rate incompatible with the hydraulic properties (conductivity) of the cerebral tissues. The autoradiographs displayed in the article show that, at low flow rate, reflux is negligible but that at around 5 µl/min, there is a leak of the liquid towards structures of the rat cortex.

DESCRIPTION OF THE INVENTION

A system for injecting and controlling a flow of liquid to be injected is firstly described, comprising:
- a peristaltic pump, for example a peristaltic micro-pump; in a particular embodiment, this may be produced using silicon technology;
- a catheter, for delivering the fluid into a tissue;
- a pressure sensor for measuring the liquid pressure in the catheter,
- control means for receiving data from the pressure sensor and for controlling the pump on the basis of data measured at different times, or on the basis of the value of an indicator, itself established on the basis of pressure measurements at different times of an operating cycle of the pump.

In particular, these means can make it possible to detect a situation of reflux during an injection and to act on the operation of the pump, for example by stopping the pump or by reversing its operation, when the pump is reversible, that is to say that it makes it possible to suck up the fluid present in the catheter. Such a system is capable of reacting rapidly to the start of a reflux along a catheter through analysis of the dynamic behaviour of the pressure measured by a sensor.

In one example, such a system may be used for the distribution of a therapeutic principle into a pathological tissue, for example into a brain tumour.

Frequently, during the delivery of a fluid into a tissue, the pressure in the catheter increases little by little, until an equilibrium is reached.

The pressure sensor makes it possible to measure the change in pressure as a function of time. The control means can determine an indicator based on a measurement of this pressure at predetermined times. For example, this indicator is a combination of different pressures observed. It can especially be a comparison between two pressure measurements, in the form of a difference or a ratio.

Generally, a peristaltic pump operates in cycles, during which the fluid is compressed, each cycle then enabling the delivery of an elementary volume of fluid. Preferably, the control means establish an indicator, associated with or relative to a same cycle, from, or on the basis of, at least two measurements of the pressure at different times of a same cycle.

The control means are then able to control the pump on the basis of the value of this indicator.

For example, the control means are able to generate an indicator on the basis of the comparison of the pressure measured at two times of a same cycle, especially on the basis of the difference between the pressures measured at two times of a same cycle.

The control means are preferably able to generate an indicator for each cycle of a series of cycles.

On the basis of the value of the indicator, the control means act on the pump, for example by interrupting its operation, or by reversing the direction of flow of the fluid. This can be done by comparing the indicator with a predetermined threshold value.

It is thus possible to detect, as quickly as possible, and to prevent, the appearance then the propagation of a reflux phenomenon, before it becomes impossible to manage (for example a contamination of the cerebrospinal fluid), the objective being to stop as quickly as possible the delivery of the product, or even to suck up part of the liquid. Thus, the indicator described above can bear witness to the presence or to the absence of a reflux.

Such a system may also make it possible to increase, by successive stages, the flow rate of the pump up to a set point determined by the user, while having available a safety mechanism which will automatically limit this flow rate as of the appearance of a start of reflux. This makes it possible to limit the consequences of the appearance of a potential reflux.

The system thus participates in an increase in the safety of the therapeutic delivery act.

Although complete management of the reflux cannot be achieved, for example due to a very great local heterogeneity of the structure of the tissue (again for example in the case of pathological cerebral parenchyma), this system enables the stoppage, as quickly as possible, of the delivery and thus the smallest contamination of the structures of the tissue or the organ concerned (in the example: the brain).

This system may be provided with a communication interface to transmit to the user the state of the system, when a start of reflux is detected, or a reduction in the flow rate, or a flow rate actually injected or a stoppage of a delivery following a critical situation. This is carried out automatically, and not manually as in the U.S. Pat. No. 7,794,443.

The invention also relates to a method for injecting and controlling the injection of a flow of liquid to be injected, comprising:
- the injection of the fluid by a peristaltic pump and a catheter;
- the measurement of the liquid pressure in the catheter by means of a pressure sensor;
- the control of the pump on the basis of the data measured by the pressure sensor at different times, or on the basis of the value of an indicator, itself established on the basis of measurements of the pressure at different times of an operating cycle of the pump.

The liquid is for example a medical liquid such as an antitumor liquid.

In such a method, it is possible to control the pump on the basis of data from the pressure sensor or the value of the indicator.

According to one embodiment, the determination of the presence or the absence of a reflux results from the calculation of an indicator established by combining at least two measurements of the pressure at different times. In the case of a cyclic pump, for example a peristaltic pump, this indicator may be calculated by combining at least two pressures observed in the course of a same cycle.

The indicator may be determined on the basis of the comparison of the pressure measured at two times of a same cycle, or instead on the basis of the difference between the pressures measured at two times of a same cycle.

Preferably, the indicator is determined for each cycle of a series of cycles.

On the basis of the value of this indicator, the control means act automatically on the pump, especially when this value indicates the appearance of a reflux phenomenon.

The detection of a reflux of the injected liquid makes it possible to reverse the direction of operation of the pump when a reflux of the injected liquid is detected.

BRIEF DESCRIPTION OF THE FIGURES

Embodiments of the invention will now be described, as non-limiting examples, while referring to the appended figures, in which:

FIG. 6 represents an enlargement of the pressure profile of FIG. 5A, FIGS. 7A-7G represent steps of operation of a micro-pump used within the scope of an embodiment of the present invention.

DETAILED DESCRIPTION OF PARTICULAR EMBODIMENTS

Figure 1:
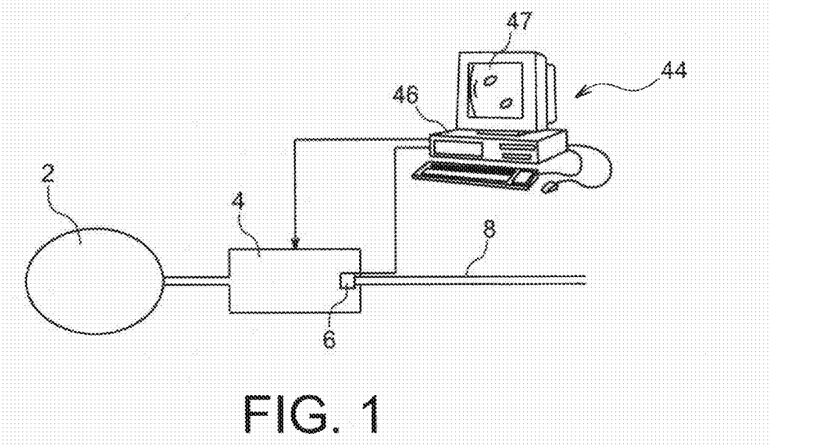
FIG. 1 represents a system being able to be implemented within the scope of the present invention.

A system represented in FIG. 1 comprises a peristaltic pump 4, for controlling the injection of a fluid through a catheter 8. This fluid itself comes from a tank 2, connected to the peristaltic pump.

A peristaltic pump makes it possible to be able to change state as quickly as possible. It has active input and output valves (electrically controllable). It is for example a MEMS pump with piezoelectric type actuation. An example of micro-pump that can be used within the scope of the present invention is described in the document WO2011/058140 and will be described in greater detail below.

Preferably, the pump has a reversible operation: it can thus manage, in the same way, a distribution of liquid, from the tank 2, to a tissue, for example a tissue of the human body or of an animal, especially the brain, and the recovery of a liquid in injection phase, from the tissue to the tank. This faculty enables the reduction of the pressure at the outlet of the catheter in a very short time. The re-pumping of a fraction of the liquid, contained in the catheter 8, makes it possible not only to block the propagation of a reflux along this same catheter, but also to re-pump all or part of the liquid forming the reflux. This is because, since a path of low hydraulic resistance is in the course of being created on the external surface of the catheter, the reverse pumping evacuates the fraction of liquid contained in the catheter, then this pocket of liquid, before beginning the removal of the liquid present in the tissues. This avoids the delivery of a liquid into an undesired place, which is a particularly important advantage when it is wished to deliver a liquid into organs such as the brain.

The adherence between the catheter and the tissue initially in contact can then be re-established if the system is left sufficient time to find a new equilibrium state.

According to one embodiment, the pumping flow rate, that is to say the flow rate of the delivered fluid, initially zero, is increased little by little. The fact of noting a reflux enables an estimation of the maximum flow rate $Q_{max}$ corresponding to the flow rate of the pump when the reflux appears. It is then understood that the fact of detecting a reflux makes it possible to adjust the pumping flow rate Q to a value less than the flow rate $Q_{max}$, the latter corresponding to the value of the flow rate having brought about a reflux.

The catheter 8 is preferably a flexible catheter and adherent to the tissues.

A pressure sensor 6 is associated with the device. As illustrated in the different variants of FIGS. 2A-2D, this sensor may be positioned in different places of the system.

In FIG. 1 (and in FIG. 2A), the sensor is incorporated in the micro-pump 4. Producing a micro-pump in silicon makes it possible to include directly the pressure sensor in the substrate of the micro-pump, as described in the application WO2011/058140.

Figure 3:
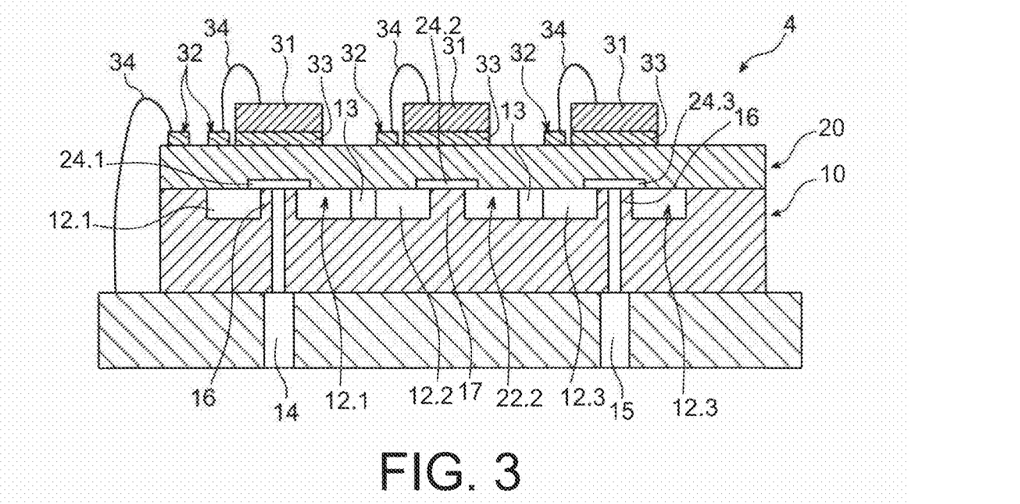
FIG. 3 represents an example of micro-pump that can be used within the scope of the present invention.

Such a pump 4 may have the structure of FIG. 3, comprising a first substrate 10 and second substrate 20 made, for example, of silicon or glass. They can have been assembled by molecular bonding or by anodic bonding.

At least 3 zones of the second substrate 20 are situated opposite at least 3 cavities 12-1, 12-2, 12-3 produced in the first substrate 10 to form deformable membranes 22-1, 22-2, 22-3. These cavities are connected in series via communication ducts 13. The central cavity 12-2 contributes to forming the pumping chamber and the two upstream 12-1 and downstream 12-3 cavities contribute to forming active valves.

Inlet 14 and outlet 15 ducts which pass through the first substrate 10 are produced in the form of wells emerging inside, respectively, the upstream 12-1 and downstream 12-3 cavities.

The inlet 14 and outlet 15 ducts emerge in said cavities via an orifice lined with an annular lip 16. The lips 16 may have a height substantially equal to the depth of the cavities in which they are situated.

At least 2 clearances 24-1, 24-3 may be formed in the lower face of the second substrate 20, and lie opposite the corresponding lips 16. They make it possible to guarantee, during the assembly of the substrates, that the top of the lips 16 does not touch the lower face of the second substrate 20.

Furthermore, these clearances 24-1, 24-3 also assure a fluid communication, in the case of a membrane not strained mechanically, between the inlet 14 and outlet 15 ducts and the cavities 12-1, 12-3 in which they emerge.

A boss 17 may be produced in the upper face of the first substrate 10 and localised substantially at the centre of the central cavity 12-2. In order to avoid contact between the top of the boss 17 and the lower face of the second substrate 20, a clearance 24-2 is advantageously formed in the latter.

In a variant, it is possible not to produce clearances in the lower face of the second substrate 20, which then remains flat. The height of the lips 16 is then less than the depth of the upstream 12-1 and downstream 12-3 cavities in which they are situated. Thus, the top of the lips 16 does not touch the lower face of the second substrate and the fluid communication, in the case of a mechanically unstrained membrane, between the inlet 14 and outlet 15 ducts and the cavities 12-1, 12-3 in which they emerge, is also assured. In the same way, it is possible to produce a boss 17, the height of which is less than the depth of the central cavity 12-2 in which it is situated.

The means for actuating these membranes may be piezoelectric means 31, positioned on conductive elements 33. Contact pads 32, conductive paths and conductive wires 34 make it possible to assure the electrical supply of the micro-pump with the external system.

Strain gauges make it possible to measure the pressure according to the present invention, via the measurement of the deformation of the membranes, as explained in WO 2011/058140. They may be realised on the upper face of the second substrate and arranged above the deformable membranes. These gauges make it possible to measure the deformation of the membranes in order to know their position (upper, lower or intermediate position), and/or to measure local pressures in the micro-channel of the micro-pump. It is for example possible to measure the pressure difference between the upstream cavity and the downstream cavity, and thus to measure the flow rate of fluid or to detect a leak. In the case where the sensor is not incorporated in the micro-pump, it may be a pressure sensor of already known type, arranged at the level of, or downstream of, the outlet channel.

The strain gauges may be made of a conductive material having a high gauge factor, for example metal, such as platinum, or, in a preferred manner, made of a doped semi-conductor material such as, for example, p-doped silicon obtained by implantation of boron ions. The implantation of boron ions may be carried out directly on the Si membrane.

Other details (dimensions, production methods) concerning this example of micro-pump are given in document WO 2011/058140. A variant of the micro-pump presented above is moreover described hereafter, with reference to FIG. 7A, details of this variant also being able to be found in document WO 2011/058140.

In all cases (that of FIG. 1 but also in FIGS. 2A-2C), the sensor 6 may be connected to a control device 44, for collecting and processing data. A control device may then control the operation of the pump 4, especially of inlet and outlet valves, on the basis of said data.

Electronic means such as a microcomputer or a calculator, comprising a central unit 46, may thus be programmed to memorise and process data from the sensor 6, for example pressure data, which is discussed later with reference to FIGS. 8A-8C. This unit may be programmed to implement a data processing method according to the invention. Display or visualisation means 47 make it possible, after processing, to represent pressure change curves, for example of the type illustrated in FIG. 4A, 5A or 6. The same means 44 can be implemented with the other configurations of the device, represented in FIGS. 2B-2C.

Figure 2A:
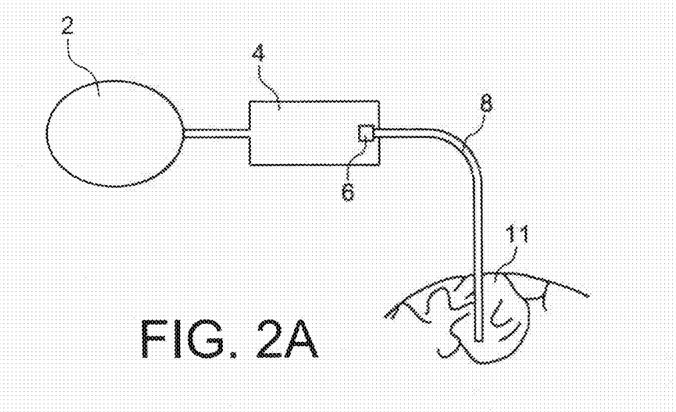
FIGS. 2A-2C represent the device of FIG. 1, and variants of this device, each time in a specific use.
Figure 2B:
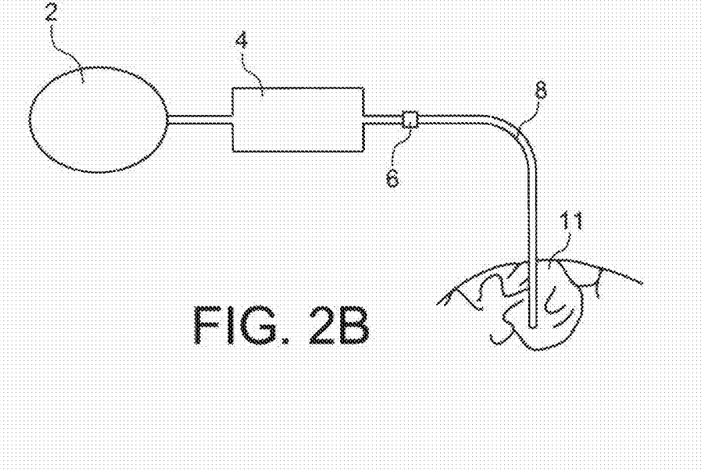
Figure 2C:
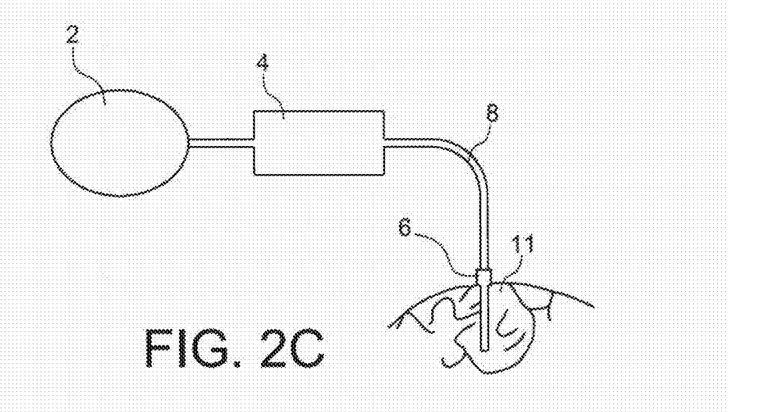

FIGS. 2A-2C represent variants of the system presented above, in an application of each of these systems to the injection of a fluid into a tissue 11, and especially into the brain. In all cases, the end of the catheter 8 is implanted in the tissue concerned, and the sensor 6 makes it possible to detect any pressure variation from the flow of the fluid in the fluid duct formed by this catheter 8.

The system represented in FIG. 2A is the same as that of FIG. 1, but during a use for an injection of a fluid into a tissue 11 of a patient by means of the catheter 8.

In FIG. 2B, the sensor 6 is positioned at the outlet of the micro-pump, but in a portion upstream of the catheter 8. Here again, the sensor may be produced using silicon technology. Arranged in the vicinity of the micro-pump, it may be incorporated in a casing common with it.

In FIG. 2C, the sensor 6 is positioned in a downstream portion of the catheter 8, but before the end thereof. It is thus an external sensor, which may be situated at the interface between the tissues 11 and the catheter 8. In certain cases, it may in fact be worthwhile placing the pressure sensor nearer to the outlet of the catheter 8, but outside of the tissues, for example just on or underneath the skin.

Thus, whatever the embodiment, it is understood that the sensor 6 is positioned, preferably, between the pump and the end of the catheter, through which the fluid is delivered. In other words, the sensor 6 is positioned downstream of the pump.

Figure 4A:
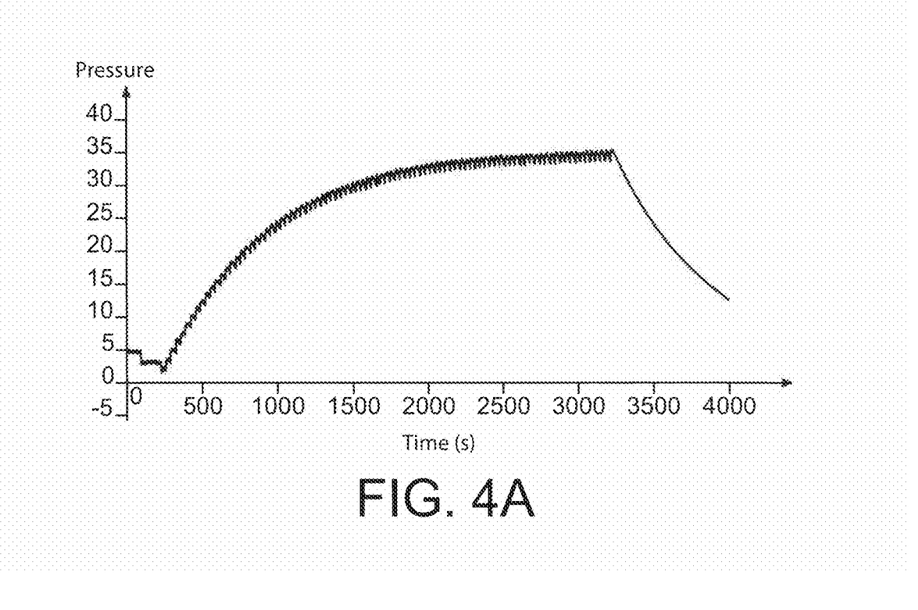
FIGS. 4A and 4B represent respectively the change in pressure during the injection of a fluid, without reflux, and a visualisation of the injection.
Figure 4B:
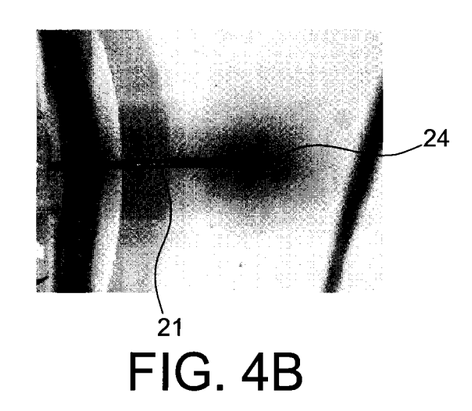

The curve of FIG. 4A represents a time recording of the change in pressure at the outlet of a micro-pump actuated by piezoelectric means, with a metal needle 21 of small diameter and in the absence of reflux. In FIG. 4B may be clearly seen the needle 21 and the medium 22 in which its end is immersed.

The parameters used for this measurement are the following:
- a 32 Gauge needle (Gauge is a unit of measure used for the diameter of needles);
- the injected liquid is a 0.6% agarose gel;
- the injection depth is 5 mm;
- the infusion volume is 10 µL;
- the injection flow rate is 0.2 µL/min;
- the pump is an MEMS type pump, with piezoelectric actuation, at a frequency of 0.025 Hz, under 170 Vpp (Volt peak–peak). The curve of FIG. 4A comprises 2 parts:
- a pressure rise, which goes substantially from the origin up to around 3200 seconds,
- then a decrease in pressure, which corresponds to the stoppage of the pump.

The representation of FIG. 4B makes it possible to visualise the injection by means of a colorant 24. This view confirms the absence of reflux, a quasi-spherical distribution of the colorant having been obtained.

Figure 5A:
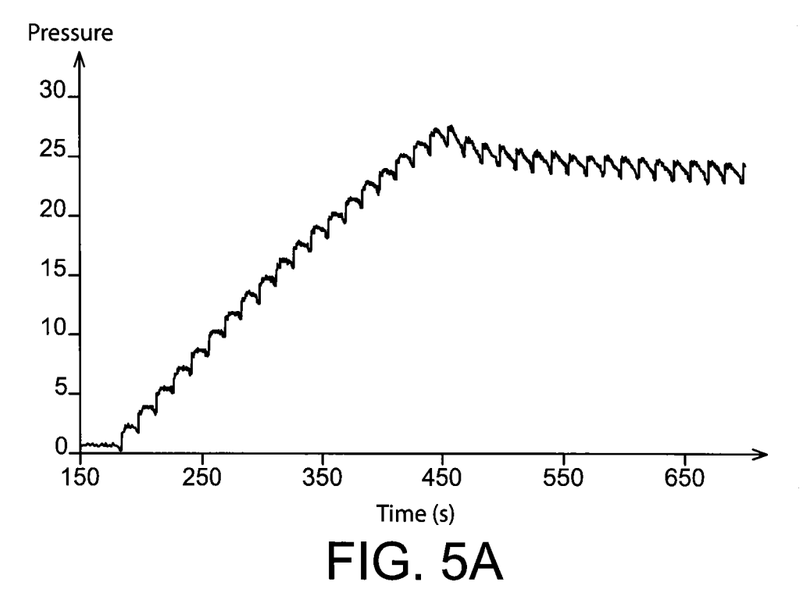
FIGS. 5A and 5B represent respectively the change in pressure during the injection of a fluid, with reflux, and a visualisation of the injection.

In the case of a reflux, the change in pressure as a function of time shows a local decrease in pressure, as the representation of FIG. 5A illustrates.

The parameters used for this measurement are the same as those for the preceding measurement, except for the latter two:
- the injection flow rate is 0.5 µL/min;
- the pump is a MEMS type pump, with piezoelectric actuation, at a frequency of 0.07 Hz, under 170 Vpp.

The curve of this FIG. 5A comprises two parts:
- a rise in pressure, which goes substantially from the origin up to around 450 seconds,
- then a slow decrease in pressure.

Figure 5B:
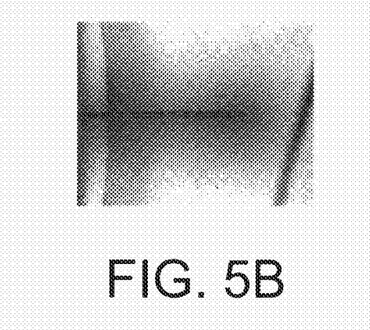
Figure 6:
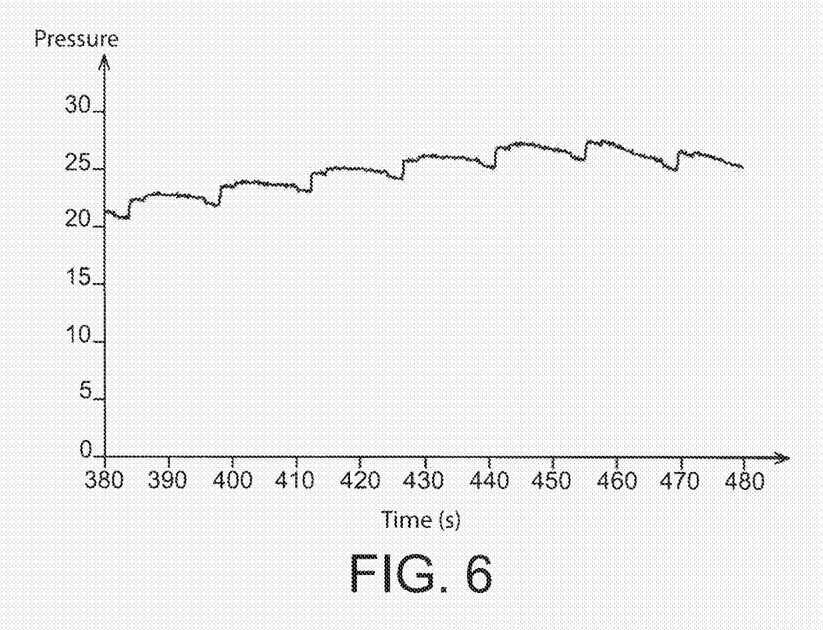

The representation of FIG. 5B again makes it possible to visualise the injection by means of a colorant 24. This view shows a distribution of the colorant localised around the needle, but with a shape far removed from the quasi-spherical shape of the distribution observed in FIG. 4B. In other words, this figure corresponds to the appearance of a reflux. FIG. 6 (for which the measurement conditions are identical to those mentioned above for FIGS. 5A and 5B) is a zoom on the period of appearance of the reflux, between 380 and 480 seconds. It shows that each pumping cycle corresponds to a flow rate pulse; thus, each pumping cycle results in a pressure pulse measured at the level of, or downstream of, the pump.

The pump 4, used in the measurements presented above, operates in periods of 6 phases according to the operating method illustrated in FIGS. 7A-7F.

Figure 7A:
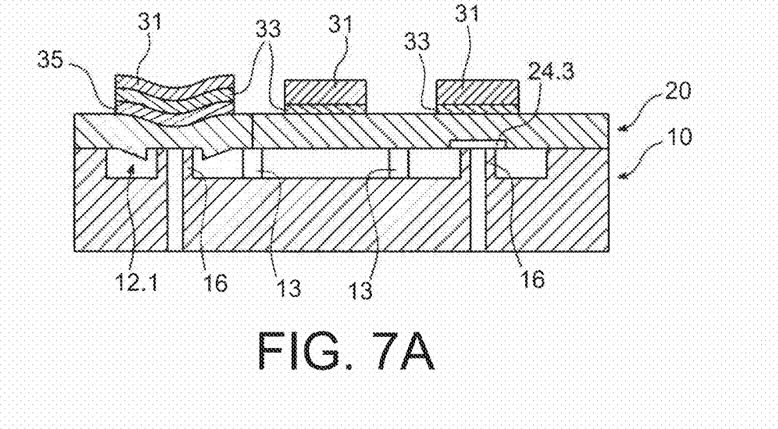

In FIG. 7A is represented an operating phase of a variant of a pump such as that described above with reference to FIG. 3.

In this variant, a strained layer 35 (FIG. 7A) is deposited directly on the surface of the upper face of at least one of the membranes produced, before the deposition of the conducting layer.

This strained layer exerts a stress on the membrane concerned, which leads to a deformation thereof. For example, this strained layer may be deposited on the upstream and downstream membranes (facing the cavities 12.1 and 12.3) and thus causes the membranes to come into contact with the lips opposite. Also, when the membranes are not activated by actuating means, here by piezoelectric pellets, the membranes are deformed in a rest position. In this way, they form upstream and downstream valves that are closed at rest. The other numerical references of FIG. 7A designate components that are identical to those that have already been described above with reference to FIG. 3 with the same numerical references.

The strained layer 35 may be, for example, $Si_3N_3$ deposited by PECVD having an internal tensile stress of the order of several hundred megapascals, for example 700 MPa. Its thickness may be of the order of 0.1 µm to 1 µm. As FIG. 7A illustrates, the deflection of the membrane 22-1 induced by the strained layer 35 is then several microns and suffices to cause the membrane to contact the opposite lip 16.

In FIG. 7A is represented the first phase of operation of the pump, this phase would be similar for the pump described above with reference to FIG. 3. During this phase, the fluid then enters via the channel 14 and exits therefrom via the channel 15.

In FIG. 7B-7F are represented different phases (respectively phases 1-6) of operation of a peristaltic pump. In this scheme, the pump is represented in a very schematic manner, with an inlet duct 14 and an outlet duct 15. The latter are placed in a different manner with respect to their positions in the structures of FIGS. 3 and 7A, but this does not change anything in the operation of the device. Also represented are the piezoelectric activation means 31 of the different chambers.

Figure 7B:
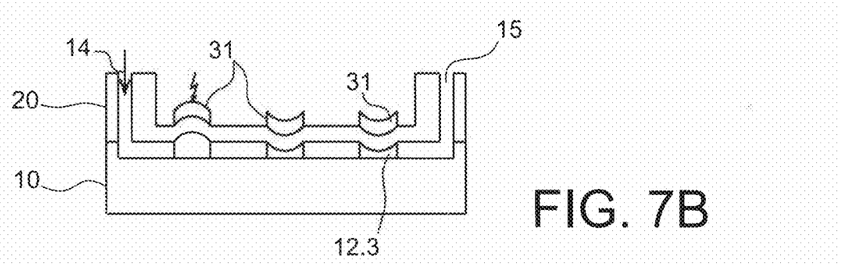
Figure 7C:
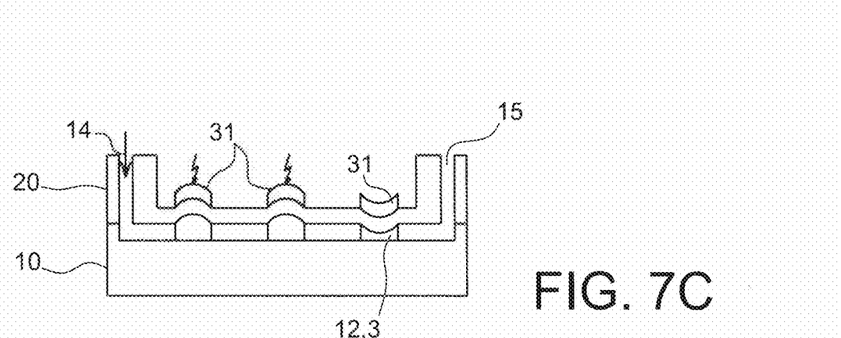
Figure 7D:
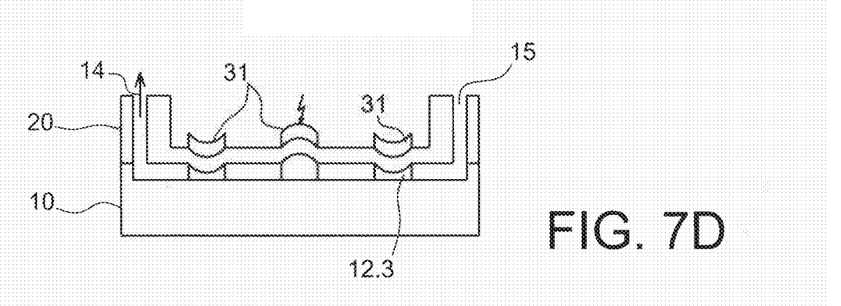
Figure 7E:
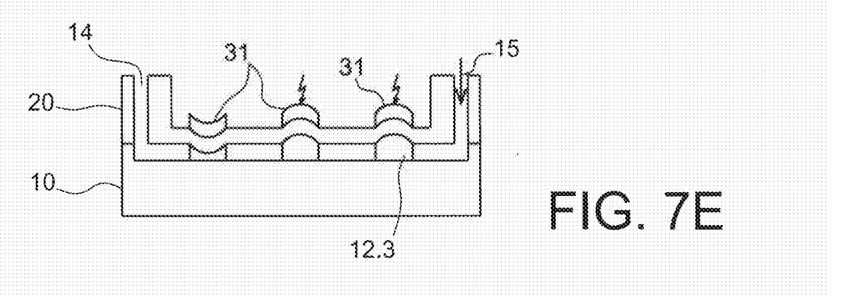

The phase of FIG. 7B (phase 1), during which the means 31 of activating the chamber 12.1 are activated, correspond to that which is represented in FIG. 7A, the fluid then entering via the channel 14.

Figure 7F:
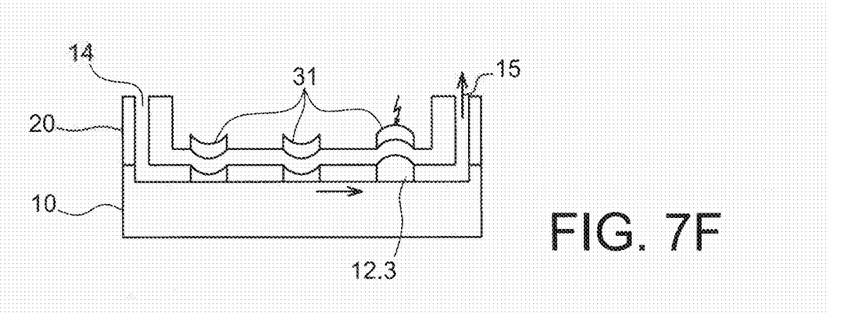
Figure 7G:
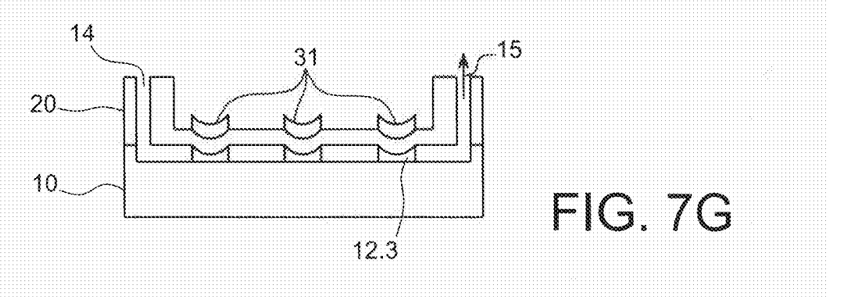

Then follow the phases, respectively, of FIGS. 7C-7G:
- activation of the means 31 of activating the chambers 12.1 and 12.2 (FIG. 7C, phase 2); the fluid then enters via the channel 14 and flows from the first chamber 12.1 to the second chamber 12.2;
- activation of the means 31 of activating the chamber 12.2 (FIG. 7D, phase 3); a very small part of the fluid is pushed back via the channel 14; This step makes it possible to form the volume of fluid to be delivered in the course of a pumping cycle;
- activation of the means 31 of activating the chambers 12.2 and 12.3 (FIG. 7E, phase 4); a very small part of fluid is sucked from the channel 15;
- activation of the means 31 of activating the chamber 12.3 (FIG. 7F, phase 5); The volume of fluid to be delivered is pushed back into the channel 15;

deactivation of all the means 31 of activating the chambers 12.1-12.3 (FIG. 7G, phase 6); the fluid continues to be still pushed back via the channel 14. This completes the back flushing of the fluid in the channel 15.

Thus, the operation of this pump is cyclic, a determined amount of fluid being delivered (pumped) during each cycle.

Peristaltic pumps generally have such a cyclic operation.

In a pump such as described above, the pressure may be measured at the outlet of the pump, that is to say that the pressure sensor 6 is located downstream of the valve 12.3. It may be added that, in the pump that has been described above, with reference to FIG. 3, the sensor makes it possible to measure the pressures in the chambers. From the moment that the outlet valve is open and that the inlet valve is closed, it makes it possible to measure the pressure in the catheter.

When the third valve 24.3 is closed (this is the case during phases 1-2-3 and 6 which correspond, respectively, to FIGS. 7A, 7B, 7C and 7G above), the pressure measured is that in the catheter. In the absence of reflux, the pressure changes little because the valve is closed. Conversely, in the presence of a reflux, this pressure reduces during these phases.

During phases 4 and 5 (which correspond to FIGS. 7E and 7F above), the valve 12.3 is open, the pressure measured increases sharply due to the injection of the volume into the catheter.

The increase in pressure is generally more pronounced in the absence of reflux.

Thus, generally speaking, a pumping cycle comprises:
- a first phase, known as rest phase, during which the pump does not deliver liquid into the catheter: during this phase, the pressure in the catheter is stable in the absence of reflux, and can decrease in the presence of a reflux. This is because, during this phase, in the absence of reflux, there is no flow of fluid in the catheter. The presence of a reflux corresponds to a leak, which can result in a decrease in pressure;
- a second phase, during which the pump injects the liquid into the catheter, which induces a pressure jump in the catheter. The presence of a reflux can result in a lessening of this pressure jump, compared to the pressure jump in the absence of reflux.

Thus, it will be understood that by measuring a pressure at different times in the course of a cycle, it is possible to establish an indicator, known as reflux indicator, from which it is possible to conclude in the presence or in the absence of a reflux. Preferably, an indicator is established relative to each cycle.

In this example, this indicator is a comparison of the pressure measured between two times of a same cycle. It will then be shown that the presence of a reflux reduces the pressure variation between the end of the period known as rest period and the start of the pumping period.

Figure 8A:
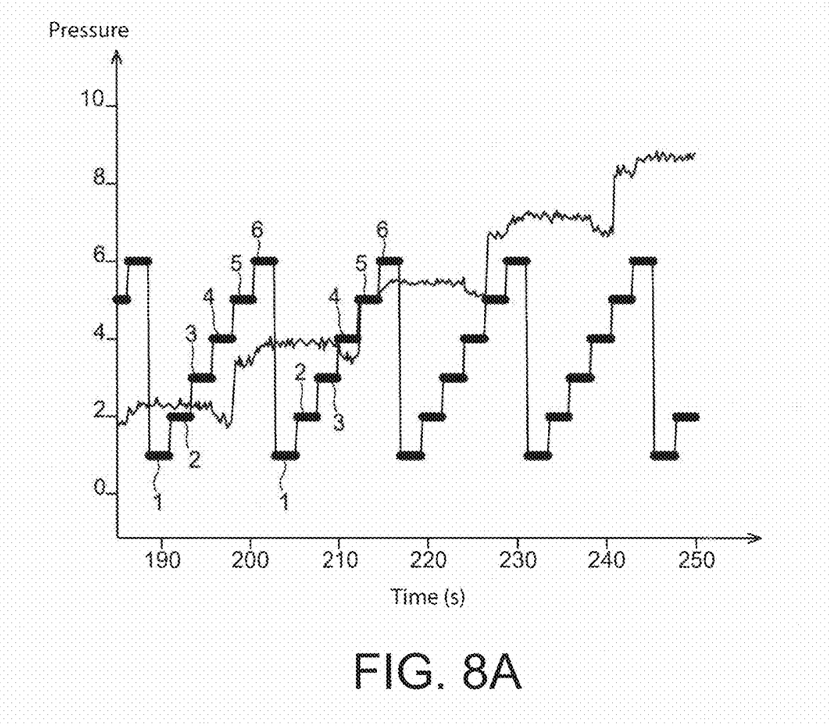
FIGS. 8A-8C represent pressure measurement curves, superimposed on the operating cycle of a micro-pump, illustrating the operating cycle of a micro-pump (FIG. 8A), the change in pressure in the case of normal injection (FIG. 8B) and the change in pressure in the case of reflux (FIG. 8C)
Figure 8B:
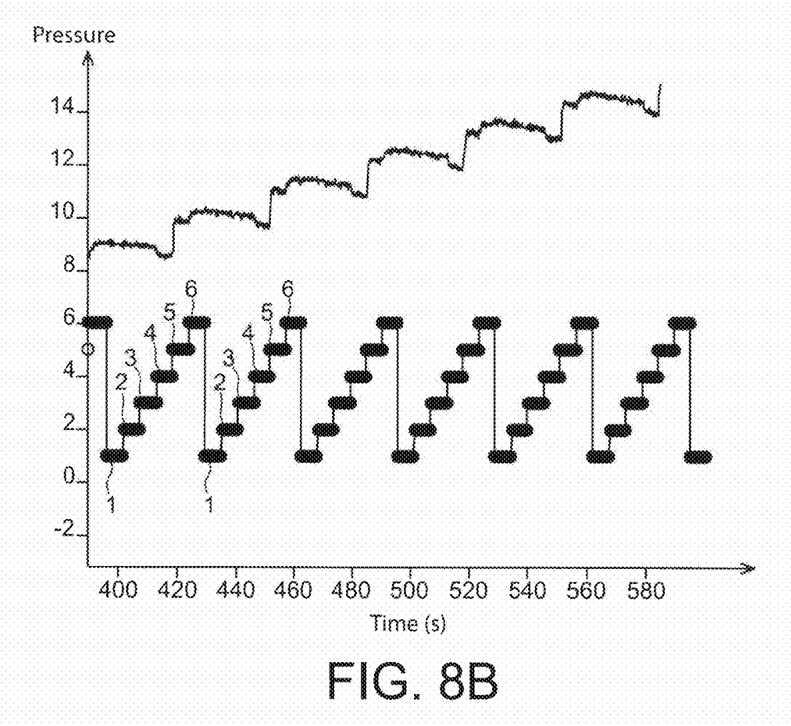
Figure 8C:
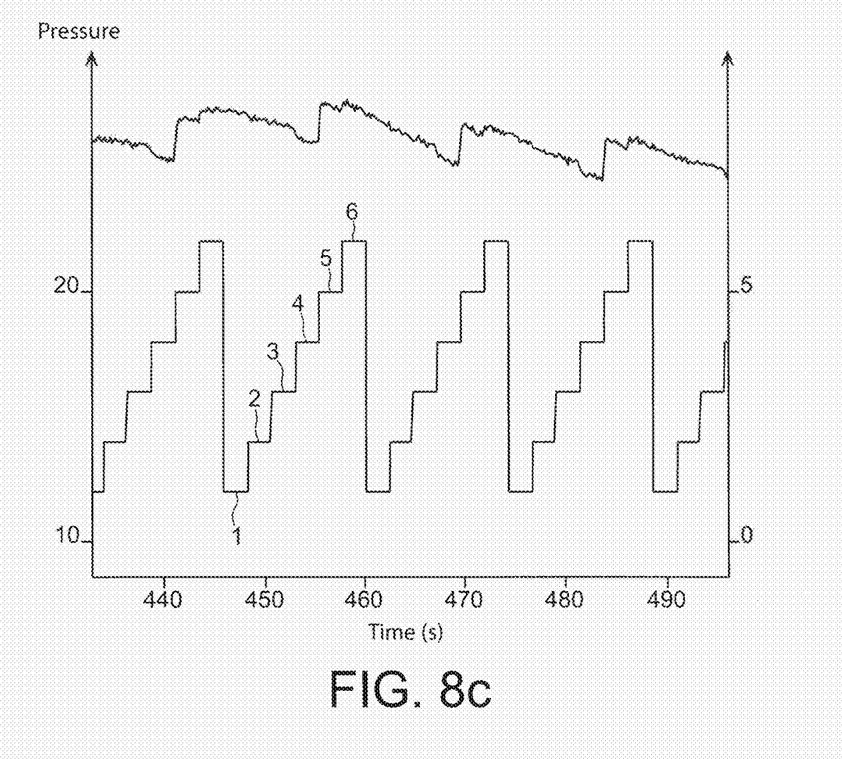

The pumping cycle is observed on the measurement curves of the pressure sensor, such as those of FIGS. 8A-8C, in which the different phases 1-6 of the first cycles are identified. The change in pressure (in arbitrary units) measured during the succession of several cycles is also represented. As described previously, this pressure changes substantially by increasing stages.

It can be clearly seen, in the curve of FIG. 8A, that, just after the start of phase 5, the liquid is injected by the pump 4, which results in an increase in pressure measured by the sensor 6. At the start of phase 6, the sensor again measures the pressure outside the pump, that is to say in the catheter: if there is no reflux, the pressure, at the start of phase 6, is slightly above that at the start of phase 5. The target tissue thus absorbs the injected liquid well. This case is illustrated in FIG. 8B, in the case of reflux, the liquid escapes from the tissue and the pressure at the start of phase 6 is the same, or even less than, that at the start of phase 5. This case is illustrated in FIG. 8C.

It is thus possible to introduce, for the considered example, the following variables:
- $P_6$: the pressure measured over a duration of, for example, 1 second after the start of phase 6,
- $P_5$: the pressure measured over a duration of, for example, 1 second after the start of phase 5.

It is thus proposed to use the following indicator to evaluate the presence of reflux:

$$J = P_6 - P_5$$

Figure 9A:
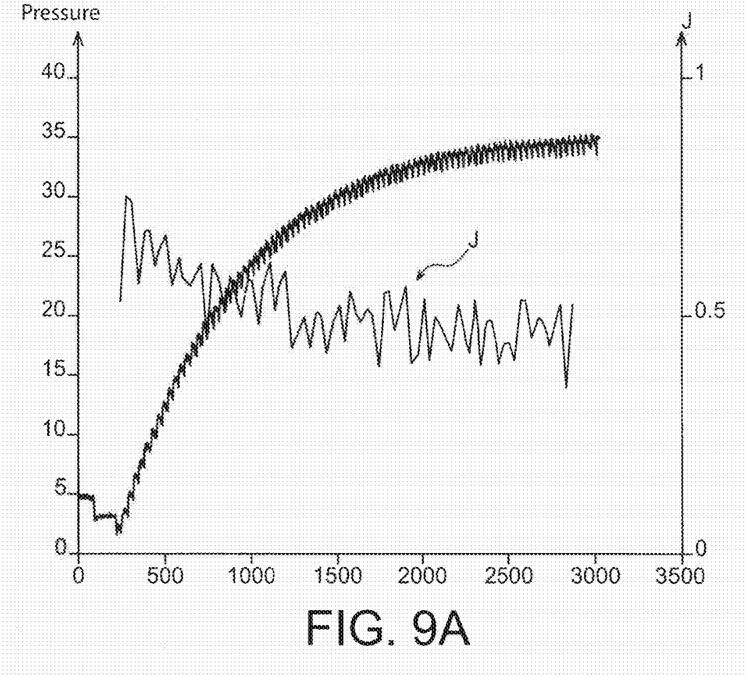
FIGS. 9A-9B represent the change of an operating parameter of the pump, in a case where there is no reflux (FIG. 9A) and in a case where there is reflux (FIG. 9B).
Figure 9B:
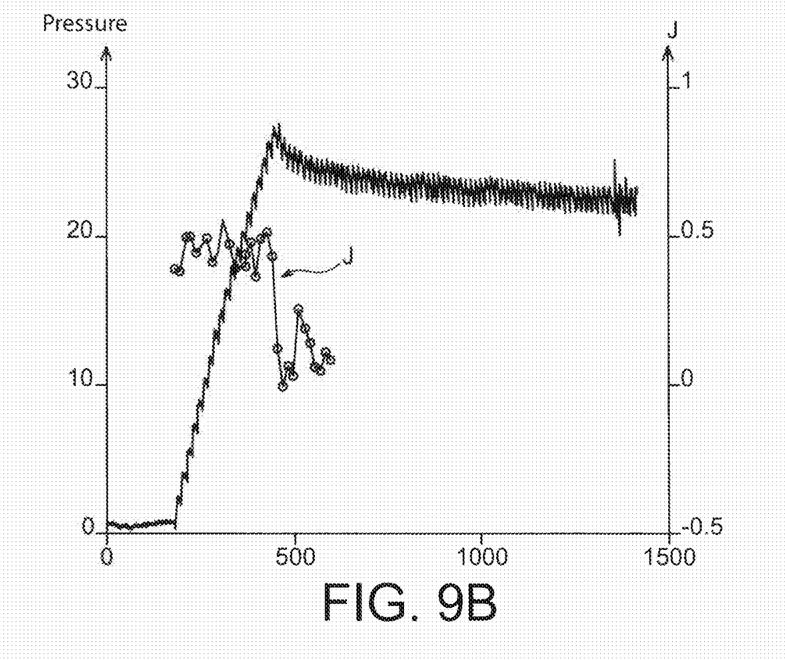

The change of this parameter is represented in FIGS. 9A and 9B (J being measured once per operating cycle of the pump):
- FIG. 9A corresponds to the case where there is no reflux, the values of J oscillate around 0.5 (right hand scale); the other curve represents the change in pressure as a function of time,
- FIG. 9B corresponds to the case where there is reflux, a drop in the value of the indicator J which may be close to 0 or even negative (right hand scale) is then observed. It will then be understood that by setting a threshold $J_{threshold}$ less than 0.5, for example between 0 and 0.2 ($0 < J_{threshold} < 0.5$), the presence of a reflux may be concluded when $J \leq J_{threshold}$.

More generally, the measurement of the pressure during different phases of operation of a pump, especially a cyclic pump and in particular a peristaltic pump, makes it possible to form an indicator J, from different pressure measurements, generally in the course of a same cycle, this indicator being representative of a reflux situation. This indicator may be, as in the example given above, the difference between the pressures measured during two final phases of the cycle of the pump, or, more generally, a difference between the pressures measured during two different phases of the cycle of the pump. The comparison of this indicator J with a predetermined threshold indicator $J_{threshold}$ then makes it possible to be able to conclude in the presence or the absence of reflux. It is then possible to establish an indicator corresponding to each cycle of a series of cycles.

The data processing means 44, 46 can, from data provided by the pump 6, calculate the parameter(s) in question, for example the parameter J as indicated above. They can also perform a comparison of this criterion J or of this, or these, parameters(s) by means of a threshold value $J_{threshold}$ in order to, optionally, trigger a stoppage of the pump 4 or a reversal of its operation. Finally, the values of the parameter retained may be presented to an operator by visualisation means 47. A reflux situation may also be signalled to him, by a visual and/or auditory signal which, once again, the means can 44,46 can produce.

In a variant of the system a micro-pump comprising passive valves is employed, that is to say valves that cannot be activated by an exterior effector. Such valves open and close under the effect of the pressure in the pump, the pumping being carried out by a valve activated, for example, by piezoelectric means. The advantage thereof is a simplification of the technology of the system and thus of the cost, but to the detriment of performance (especially in terms of safety). It is then in fact impossible to reduce the pressure in the fluid circuit of the pump, only the rapid stoppage of the injection would be possible. Furthermore, this type of valve does not make it possible to operate according to a reversible mode.

The reflux indicator J may be determined simply, for example by comparing two values measured at two different times, as explained above.

But, generally speaking, more complex indicators may be envisaged, from pressure values at different times.

The invention may be implemented within the scope of any application requiring the localised injection, by means of a catheter, of a liquid, for example a therapeutic antitumor liquid, especially into an organ of not very compact structure (for example analogous to the brain).

Thus, an insertion of a catheter may be made into a tissue 11 of a patient (or, more generally, of a living mammal), as illustrated in each of FIGS. 2A-2C, this catheter having been, or then being, connected to an assembly comprising a pump 4 and a sensor 6 such as described above, all of these then being able to be connected to a tank 2 of a liquid to be injected into the tissue 11. These steps are preceded by a surgical step to introduce the catheter into the tissue.

The invention claimed is:

1. A system for injecting and controlling a flow of liquid to be injected, comprising:
    a catheter, comprising a duct extending from a peristaltic pump toward where the liquid is to be injected, for delivering the liquid to be injected;
    the peristaltic pump operating in cycles, each cycle including plural phases for generating increases in pressure, such that an elementary volume of the liquid is delivered during each cycle;
    a pressure sensor measuring liquid pressure at a position on the duct outside the peristaltic pump;
    a controller configured to receive data from the pressure sensor, and generate a reflux indicator, relative to a cycle, on the basis of at least two measurements of the pressure at different phases of the cycle, the different phases of the cycle being associated with successive intended increases in pressure generated by the peristaltic pump and being phases when the liquid is delivered through the catheter;
    said controller configured to control the peristaltic pump on the basis of a value of the reflux indicator,
    wherein the controller is configured to generate the reflux indicator when a difference in the pressure measured at two phases of the cycle is below a threshold indicating the intended increase in pressure between the two phases.

2. A system according to claim 1, wherein the pressure sensor is arranged between the peristaltic pump and an end of the duct through which the liquid is delivered.

3. A system according to claim 1, wherein the controller is configured to generate the reflux indicator for each cycle of a series of cycles.

4. A system according to claim 1, wherein said controller is configured to stop or reverse an operation of the peristaltic pump on the basis of data measured by the pressure sensor.

5. A system according to claim 1, wherein the peristaltic pump is a peristaltic micro-pump.

6. A system according to claim 1, wherein said controller is configured to control a flow rate, to increase or to reduce the flow rate of the peristaltic pump on the basis of the value of the reflux indicator.

7. The system according to claim 1, wherein the controller is configured to generate the reflux indicator by
    calculating a parameter by subtracting liquid pressure measured by the pressure sensor at a first phase of the cycle from liquid pressure measured by the pressure sensor at a second phase of the cycle, the second phase occurring after the first phase within the cycle, and
    generating the reflux indicator when the calculated parameter is below the threshold.

8. A method for injecting and controlling a flow of liquid to be injected, comprising:
    injecting the liquid by a peristaltic pump and a catheter comprising a duct extending from the peristaltic pump toward where the liquid is to be injected, the peristaltic pump operating in cycles, each cycle including plural phases for generating increases in pressure, such that an elementary volume of the liquid is delivered during each cycle;
    measuring liquid pressure in the duct by a pressure sensor located on the duct outside the peristaltic pump;
    calculating a reflux indicator, relative to a cycle, on the basis of at least two measurements of the pressure at different phases of the cycle, the different phases of the cycle being associated with successive intended increases in pressure generated by the peristaltic pump and being phases when the liquid is delivered through the catheter;
    controlling the peristaltic pump on the basis of the reflux indicator, wherein
    the reflux indicator is generated when a difference in the pressure measured at two phases of the cycle is below a threshold indicating the intended increase in pressure between the two phases.

9. A method according to claim 8, wherein the step of measuring liquid pressure is carried out between the peristaltic pump and an end of the duct through which the liquid is delivered.

10. A method according to claim 8, wherein the reflux indicator is determined for each cycle of a series of cycles.

11. A method according to claim 8, wherein a direction of operation of the peristaltic pump is reversed when a reflux of the injected liquid is detected.

12. A method according to claim 8, wherein the peristaltic pump is a peristaltic micro-pump or a passive check valve micro-pump.

13. A method according to claim 8, wherein the liquid is a medical liquid, or an antitumor liquid.

* * * * *